US010368792B2

(12) United States Patent
Keshava et al.

(10) Patent No.: US 10,368,792 B2
(45) Date of Patent: Aug. 6, 2019

(54) METHOD FOR DETECTING DECEPTION AND PREDICTING INTERVIEWER ACCURACY IN INVESTIGATIVE INTERVIEWING USING INTERVIEWER, INTERVIEWEE AND DYADIC PHYSIOLOGICAL AND BEHAVIORAL MEASUREMENTS

(71) Applicant: The Charles Stark Draper Laboratory, Inc., Cambridge, MA (US)

(72) Inventors: Nirmal Keshava, Needham, MA (US); Andrea K. Webb, Medford, MA (US); Laura J. Mariano, Belmont, MA (US); Philip D. Parks, Jamaica Plain, MA (US); Joshua C. Poore, Cambridge, MA (US)

(73) Assignee: THE CHARLES STARK DRAPER LABORATORY INC., Cambridge, MA (US)

( * ) Notice: Subject to any disclaimer, the term of this patent is extended or adjusted under 35 U.S.C. 154(b) by 648 days.

(21) Appl. No.: 14/728,527

(22) Filed: Jun. 2, 2015

(65) Prior Publication Data
US 2016/0354024 A1    Dec. 8, 2016

(51) Int. Cl.
*A61B 5/16*    (2006.01)
*A61B 5/0205*    (2006.01)
(Continued)

(52) U.S. Cl.
CPC ............ *A61B 5/164* (2013.01); *A61B 5/0077* (2013.01); *A61B 5/0205* (2013.01);
(Continued)

(58) Field of Classification Search
CPC ....... A61B 5/16; A61B 5/0402; A61B 5/0205; A61B 5/04; A61B 5/0077; A61B 5/0404;
(Continued)

(56) References Cited

U.S. PATENT DOCUMENTS

| 8,543,196 B2 | 9/2013 | Ning |
| 8,992,227 B2 | 3/2015 | Al Bandar et al. |
| (Continued) | | |

FOREIGN PATENT DOCUMENTS

EP        2932899 A1 *  10/2015  ............... A61B 5/11

OTHER PUBLICATIONS

Escalera et al. "Modelling and analyzing multimodal dyadic interactions using social networks", In: International Conference on Multimodal Interfaces and the Workshop on Machine Learning for Multimodal Interaction. New York, NY, USA: ACM, ICMI-MLMI'10, pp. 52:1-52:8. URL http://doi.acm.org/10.1145/1891903.1891967.*

(Continued)

*Primary Examiner* — Eddy Saint-Vil
(74) *Attorney, Agent, or Firm* — Christopher J. McKenna; Foley & Lardner LLP (57) ABSTRACT

Existing approaches for deception detection are primarily based on polygraph systems that measure specific channels of physiology in highly structured interviews and that are interpreted by trained polygraph examiners. Existing approaches for predicting interviewer accuracy involve interviewers' own estimates of their performances which inevitably are biased. The methods and systems described herein provides objective, quantitative and automated metrics to detect deception and predict interviewer accuracy. Physiological information of the interviewer during the interview is recorded by at least a first sensor. The physiological information includes a time series of physiological data. An interview assessment is calculated by a computer. By processing the recorded physiological information, the interview assessment indicates at least one of whether a statement made by the interviewee is likely to be deceitful and whether the interviewer is likely to be accurate in (Continued)

estimating truthfulness of the interviewee. The interview assessment is output by the computer.

18 Claims, 4 Drawing Sheets

(51) Int. Cl.
| | | |
|---|---|---|
| A61B 5/04 | (2006.01) | |
| A61B 5/0402 | (2006.01) | |
| A61B 5/11 | (2006.01) | |
| A61B 5/00 | (2006.01) | |
| A61B 5/0404 | (2006.01) | |
| A61B 5/053 | (2006.01) | |
| A61B 5/1455 | (2006.01) | |
| A61B 5/08 | (2006.01) | |

(52) U.S. Cl.
CPC .......... *A61B 5/0404* (2013.01); *A61B 5/0533* (2013.01); *A61B 5/1128* (2013.01); *A61B 5/0402* (2013.01); *A61B 5/0816* (2013.01); *A61B 5/11* (2013.01); *A61B 5/14551* (2013.01); *A61B 5/14552* (2013.01); *A61B 5/6823* (2013.01); *A61B 5/6824* (2013.01); *A61B 5/6828* (2013.01); *A61B 5/6829* (2013.01)

(58) Field of Classification Search
CPC ....... A61B 5/0533; A61B 5/0816; A61B 5/11; A61B 5/1128; A61B 5/14551; A61B 5/14552

See application file for complete search history.

(56) References Cited

U.S. PATENT DOCUMENTS

| | | | | |
|---|---|---|---|---|
| 10,019,681 | B2* | 7/2018 | Scriffignano | G06Q 10/067 |
| 2004/0143170 | A1* | 7/2004 | DuRousseau | A61B 5/16 |
| | | | | 600/300 |
| 2005/0246165 | A1* | 11/2005 | Pettinelli | G10L 15/1807 |
| | | | | 704/207 |
| 2007/0038035 | A1* | 2/2007 | Ehrlich | A61B 5/16 |
| | | | | 600/300 |
| 2007/0213981 | A1* | 9/2007 | Meyerhoff | G10L 17/26 |
| | | | | 704/243 |
| 2012/0116186 | A1* | 5/2012 | Shrivastav | A61B 5/0507 |
| | | | | 600/301 |
| 2013/0139254 | A1* | 5/2013 | Tegreene | A61B 5/16 |
| | | | | 726/22 |
| 2015/0007037 | A1* | 1/2015 | Butler | H04L 41/22 |
| | | | | 715/736 |
| 2016/0143570 | A1* | 5/2016 | Valacich | G06F 21/316 |
| | | | | 434/362 |

OTHER PUBLICATIONS

Xiang et al., "Is Interactional Dissynchrony a Clue to Deception? Insights from Automated Analysis of Nonverbal Visual Cues", IEEE Transactions on Cybernetics Jan. 2013.*

Narayanan "Behavioral Signal Processing: Enabling human-centered behavioral informatics", May 2015.*

Sanaz Rezaei, Physiological Synchrony as Manifested in Dyadic Interactions, Jun. 2013.*

Neha Gada, Beyond the Handshake: Intentional Synchrony Effects on Job Interview, Jun. 1999.*

Bernieri, F. J., et al. "Interpersonal coordination: Behavior matching and interactional synchrony." In R. S. Feldman & B. Rimé (Eds.), Fundamentals of nonverbal behavior (pp. 401-432). Cambridge: Cambridge University Press. (1991).

Burgoon, Judee K., et al. "Interpersonal deception: III. Effects of Deceit on Perceived Communication and Nonverbal Behavior Dynamics," Journal of Nonverbal Behavior, vol. 18, Issue 2, pp. 155-184 (summer 1994) (http://link.springer.com/article/10.1007/BF02170076#).

Harrison, Albert A., et al, "Cues to Deception in an Interview Situation," Social Psychology vol. 41, No. 2, pp. 156-161 (Jun. 1978) http://www.jstor.org/discover/10.2307/3033575?uid=3739656 &uid=2&uid=4&uid=3739256&sid=21104531395341).

Tower, Debra L., et al, "Don't Lie to Me: The Impact of Deception on Vocalic and Linguistic Synchrony," 2013 European Intelligence and Security Informatics Conference (EISIC), pp. 262-265, Aug. 12-14, 2013 (http://ieeexplore.ieee.org/xpl/login.jsp?tp=&arnumber=6657178&&url=http%3A%2F%2Fieeexplore.ieee.org%2Fxpls%2Fabs_all.jsp%3Farnumber%3D6657178).

Vrij Aldert, et al, Insight Into Behavior Displayed During Deception, Human Communication Research, vol. 22, No. 4, pp. 544-562 (Jun. 1996) (http://onlinelibrary.wiley.com/doi/10.1111/j.1468-2958.1996.tb00378.x/abstract;jsessionid=7A3D7EBD7F66F7E5DF11F153B86902D5.f01t01 ).

Yu, Xiang, et al. "Automated Analysis of Interactional Synchrony using Robust Facial Tracking and Expression Recognition," 10th IEEE International Conference and Workshops on Automatic Face and Gesture Recognition (FG), Apr. 22-26, 2013 (http://ieeexplore.ieee.org/xpls/abs_all.jsp?arnumber=6553802).

* cited by examiner

METHOD FOR DETECTING DECEPTION AND PREDICTING INTERVIEWER ACCURACY IN INVESTIGATIVE INTERVIEWING USING INTERVIEWER, INTERVIEWEE AND DYADIC PHYSIOLOGICAL AND BEHAVIORAL MEASUREMENTS

FEDERALLY SPONSORED RESEARCH

This invention was made with government support under FA8650-12-C7210 awarded by the Department of the Air Force. The government has certain rights in the invention.

BACKGROUND

Deception detection continues to be a challenge for law enforcement and the intelligence community. Experts have concerns over traditional polygraph-based approaches. More objective measures are needed to detect interviewee's deception and predict interviewer's accuracy.

SUMMARY

One aspect of the disclosure relates to a method of detecting deception by an interviewee and predicting accuracy by an interviewer in an interview conducted by the interviewer. According to the method, physiological information of the interviewer during the interview is recorded by at least a first sensor. The physiological information includes a time series of physiological data. An interview assessment is calculated by a computer by processing the recorded physiological information. The interview assessment indicates at least one of whether a statement made by the interviewee is likely to be deceitful and whether the interviewer is likely to be accurate in estimating truthfulness of the interviewee. The interview assessment is output by the computer.

In some implementations, the physiological data includes at least one of electrocardiogram data, skin conductance data, and pulse oximetry data. In some implementations, the physiological data includes a time series of electrocardiogram recordings of the interviewer, and processing the physiological information includes at least one of calculating a level of entropy of the electrocardiogram recordings, a heart rate, and time intervals between consecutive normal sinus beats.

In some implementations, the method further includes recording by at least a second sensor physiological information of the interviewee during the interview. According to the method, processing the physiological information includes performing dyadic analysis of the recorded physiological information of the interviewer with the recorded physiological information of the interviewee. In some implementations, the dyadic analysis includes applying an auto-regressive integrated moving average analysis to the physiological information of the interviewer and the interviewee, and determining at least one of an influence relationship between changes in the physiological information of interviewer and the interviewee and a degree of coherence between the physiological information of interviewer and the interviewee.

In some implementations, calculating the interview assessment further includes determining by the computer at least one of an influence relationship and a level of coherence between bodily motions of the interviewer and the interviewee. In some implementations, the method includes recording video of the interview and processing the recorded video to generate an interviewer bodily motion time series and an interviewee bodily motion time series. In some implementations determining by the computer at least one of the influence relationship and the level of coherence between bodily motions of the interviewer and the interviewee includes processing the interviewer bodily motion time series and the interviewee bodily motion time series. In some implementations, the interviewer bodily motion time series and the interviewee bodily motion time series indicate times at which the interviewer and interviewee, respectively, moved their respective limbs or appendages. In some implementations, the determining by the computer at least one of an influence relationship and a level of coherence between bodily motions of the interviewer and the interviewee includes modelling the bodily motions of the interviewer and interviewee as a coupled Hidden Markov Model.

Another aspect of the disclosure relates to a system for detecting deception by an interviewee and predicting accuracy by an interviewer in an interview conducted by the interviewer, including a first sensor, a processor, and an output device. The first sensor is configured to record physiological information of the interviewer during the interview. The physiological information includes a time series of physiological data. The processor is configured to calculate an interview assessment by processing the recorded physiological information. The interview assessment indicates at least one of whether a statement made by the interviewee is likely to be deceitful and whether the interviewer is likely to be accurate in estimating truthfulness of the interviewee. The output device is configured to output the interview assessment.

In some implementations, the physiological data includes at least one of electrocardiogram data, skin conductance data, and pulse oximetry data. In some implementations, the physiological data includes a time series of electrocardiogram recordings of the interviewer, and processing the physiological information comprises at least one of calculating a level of entropy of the electrocardiogram recordings, a heart rate, and time intervals between consecutive normal sinus beats.

In some implementations, the system further includes at least a second sensor configured to record physiological information of the interviewee during the interview. According to the system, when the processor processes the physiological information, the processor is configured to perform dyadic analysis of the recorded physiological information of the interviewer with the recorded physiological information of the interviewee.

In some implementations, when the processor performs dyadic analysis, the processor is configured to apply an auto-regressive integrated moving average analysis to the physiological information of the interviewer and the interviewee, and determine at least one of an influence relationship between changes in the physiological information of interviewer and the interviewee and a degree of coherence between the physiological information of interviewer and the interviewee. In some implementations, when the processor performs dyadic analysis, the processor is configured to apply an auto-regressive integrated moving average analysis to the physiological information of the interviewer and the interviewee, and determine at least one of an influence relationship between changes in the physiological information of interviewer and the interviewee and a degree of coherence between the physiological information of interviewer and the interviewee.

In some implementations, when the processor calculates the interview assessment, the processor is configured to further determine at least one of an influence relationship and a level of coherence between bodily motions of the interviewer and the interviewee. In some implementations, the system further includes a video recording device configured to record a video of the interview and process the recorded video to generate an interviewer bodily motion time series and an interviewee bodily motion time series. According to the system, when the processor determines at least one of the influence relationship and the level of coherence between bodily motions of the interviewer and the interviewee, the processor is configured to process the interviewer bodily motion time series and the interviewee bodily motion time series. In some implementations, the interviewer bodily motion time series and the interviewee bodily motion time series indicate times at which the interviewer and interviewee, respectively, moved their respective limbs or appendages. In some implementations, when the processor determines at least one of the influence relationship and the level of coherence between bodily motions of the interviewer and the interviewee, the processor is configured to model the bodily motions of the interviewer and interviewee as a coupled Hidden Markov Model.

Still another aspect of the disclosure relates to non-transitory computer readable medium storing a computer-readable program of detecting deception by an interviewee and predicting accuracy by an interviewer in an interview conducted by the interviewer. The program includes computer-readable instructions to record, from at least a first sensor, physiological information of the interviewer during the interview, wherein the physiological information includes a time series of physiological data; computer-readable instructions to calculate an interview assessment by processing the recorded physiological information, the interview assessment indicating at least one of whether a statement made by the interviewee is likely to be deceitful and whether the interviewer is likely to be accurate in estimating truthfulness of the interviewee; and computer-readable instructions to output the interview assessment.

In some implementations, the non-transitory computer readable medium further includes computer-readable instructions to record, from at least a second sensor, physiological information of the interviewee during the interview. Processing the physiological information includes performing dyadic analysis of the recorded physiological information of the interviewer with the recorded physiological information of the interviewee.

In some implementations, calculating the interview assessment further includes determining by the computer at least one of an influence relationship and a level of coherence between bodily motions of the interviewer and the interviewee.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and methods described herein provide decision support to an investigative interviewer. A decision support tool leverages measurements obtained from the interviewer and an interviewee to detect deception with improved consistency. The tool can also provide an assessment regarding the accuracy of an interviewer's personal assessment of the interviewee's deceptiveness.

Figure 1:
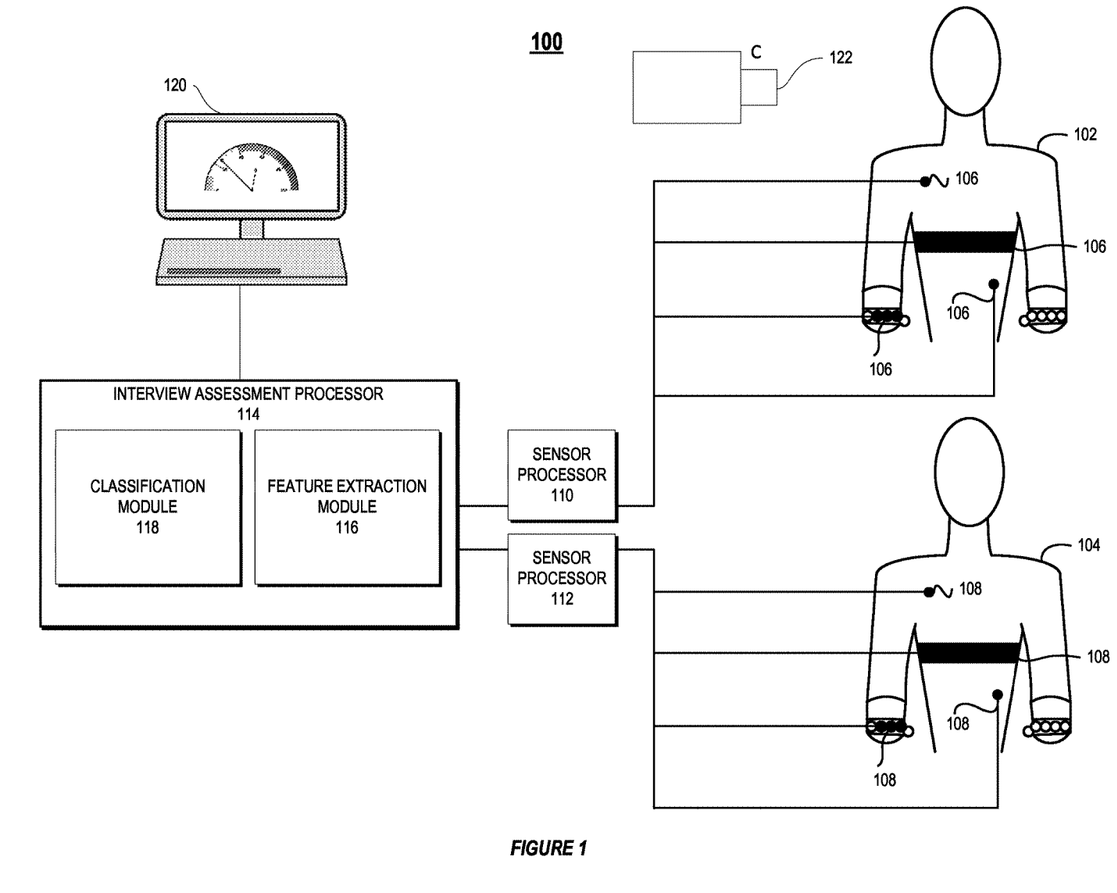
FIG. 1 illustrates a schematic diagram of an example interview assessment system for detecting deception and predicting interviewer accuracy.

FIG. 1 illustrates a schematic diagram of an example interview assessment system 100 for detecting deception and predicting interviewer accuracy. The interview assessment system 100 includes a plurality of sensors 106 and 108 which are coupled to an interviewer 102 and an interviewee 104, and which record physiological and bodily movement data from the interviewer 102 and the interviewee 104. The system 100 also includes sensor processors 110 and 112, an interview assessment processor 114, an output device 120, and a video camera system 122.

The system 100 includes a plurality of sensors 106 and 108 that are coupled to the interviewer 102 and the interviewee 104. The sensors 106 and 108 record a plurality of physiological and bodily movement signals from the interviewer 102 and the interviewee 104. In some implementations, the sensors 106 and 108 in conjunction with the sensor processors 110 and 112 are configured to monitor and record a plurality of different physiological and bodily movement signals, such as, but not limited to, heart activity, brain activity, respiration, skin conductance, and bodily movements. For example, the sensors 106 and 108 can include electrocardiographic (ECG) electrodes to allow the sensor processors 110 and 112 record measurements of heart rate, inter-heartbeat interval (IBI), and intervals between consecutive normal sinus beats (NN); electroencephalograph (EEG) electrodes to allow the sensor processors 110 and 112 measure and record brain activity; pneumography sensors coupled around the interviewer's and/or the interviewee's chest to allow the sensor processors 110 and 112 to measure respiration rate; motion sensors (e.g., accelerometers and/or gyroscopes) placed on the interviewer's or the interviewee's arms, hand, legs and/or feet to allow the sensor processors 110 and 112 record limb or appendage movements; pulse oximeter sensors coupled to the fingers of the interviewer 102 or the interviewee 104 to allow the sensor processors 110 and 112 to measure blood oxygen level, pulse rate, and blood pressure. While any of the above physiological or bodily signals may be used to detect deception and predict interviewer accuracy, for ease of description, the remainder of this description will primarily focus on a discussion of the use of ECG bodily movement signals.

The interview assessment system 100 also includes a plurality of sensor processors 110 and 112. The sensor processors 110 and 112 are configured to receive raw sensor data from the plurality of the sensors 106 and 108 coupled to the interviewer 102 and the interviewee 104 and convert and process the received sensor data if needed. For example, the sensor processors 110 and 112 can convert analog waveform ECG data to digital data and then process the digital data to obtain useful physiological information, such as heart rate, an inter-heartbeat interval (IBI), and intervals between consecutive normal sinus beats. In some implementations, the sensor processors 110 and 112 include a plurality of inputs to simultaneously receive data from multiple or all of the plurality of sensors 106 and 108.

The sensor processors 110 and 112 have a resolution of 8, 12, 16, 32, 64, or more bits. In some implementations, the sensor processors 110 and 112 may sample the data at about 128 Hz, at about 256 Hz, at about 512 Hz, at about 1024 Hz, at about 2024 Hz, or a higher sampling rate (for example at about the Nyquist rate of the signal being digitized). In some implementations, the sensor processors 110 and 112 are configured to digitize the signals received at each of its ports at different sampling rates responsive to the Nyquist rate of each of the signals. For example, respiration rate (with a relatively low Nyquist rate) may be recorded at a lower frequency than heart rate (with a relatively higher Nyquist rate). In some implementations, the sensor processors 110 and 112 filter the data (e.g., with a low pass or notch filter) to remove noise (or other artifacts) from the signals coming from the sensors 106 and 108.

In some implementations, the sensor processors 110 and 112 are external to the interview assessment system 100. For example, the sensor processors 110 and 112 may be components of standalone data acquisition systems that receive data from the plurality of sensors 110 and 112 and then supply the data in a digital format to the interview assessment system 100 through a USB, optical, or other digital connection. For example, the sensor processor 110 or 112 may be a component of a BIOPAC (headquartered in Goleta, California) or National Instruments (headquartered in Austin, Texas) data acquisition system. In some implementations, the sensor processors 110 and 112 can be standard medical multimonitors. In other implementations, the sensor processors 110 and 112 record and save the sensor data from the sensors 106 and 108. The data is later provided to the interview assessment system 100 for "off-line" analysis at a time after the recording of the data.

The interview assessment system 100 also includes an interview assessment processor. The interview assessment processor includes a feature extraction module 116 and a classification module 118. The interview assessment processor is discussed further in relation to FIG. 2. Briefly, the interview assessment processor collects one or more physiological and bodily movement signals from the interviewer 102 and the interviewee 104 through the sensor processors 110 and 112. In some implementations, the physiological signals includes ECG data (e.g., heart rate and inter-heartbeat interval data), skin conductance data, pulse oximetry data, respiratory data, EEG, or any combination thereof. The feature extraction module 116 extracts features from the physiological and the bodily movement signals. The extracted features are sent to the classification module 118.

The classification module classifies whether the interviewee was being deceitful and/or whether the interviewer was accurately assessing the interviewee's deceptiveness. In some implementations, the classification result is a binary decision. In some implementations, the classification result is a probability or a likelihood value. In some implementations, the assessments are associated with periods of time during the interview and may not be directly tied to a specific question, answer, or interviewee deceptiveness decision.

The interview assessment system 100 also includes an output device 120. The result of the classification module is sent to the output device. In some implementations, the output device is a display that is attached to the same computer that hosts the interview assessment processor or to a computer in communication with the interview assessment processor over a network (e.g., a local area work or a wide area network). In some implementations, the output device is a mobile device, such as a smartphone. In other implementations, the output device is an audio device or other visual output device. The output can be in various forms. For example, the output can take the form of a warning message, a set of colors and indicators, or audio outputs (e.g., alarm signals, or tones indicating increased deceptiveness or decreased accuracy). Other examples of the output include, but are not limited to, graphical displays of gauges, charts, dashboards, and a plurality of metrics corresponding to various assessments from the interviewer and the interviewee. For example, as shown in FIG. 1, the output device 120 can display a graphical gauge. The gauge indicates the range (0% to 100%) of probability that the interviewee is being deceitful. One end of the dial indicates a low probability that the interviewee was or is being deceitful. The other end of the dial indicates a high probability that the interviewee was or is being deceitful. The output can include two indicators (e.g., gauges and bars), one indicating the current determined deception assessment and the other indicating interviewer accuracy. An interviewer can review the indicators to change questioning tactics and improve his self-awareness during the interview. In some implementations, the output device 120 and the interview assessment processor 114 are connected via a wireless network.

The interview assessment system 100 also includes a video camera system 122, which includes at least one video camera. The video camera system 122 records the physiological and bodily movement information of the interviewer 102 and the interviewee 104. The information is sent to the interview assessment processor 114. In some implementations, the physiological information includes, but is not limited to, pupil diameter. In some implementations, bodily movement information includes head, leg, arm, hand or feet movements, and changes in gaze direction. In other implementations, other information, such as speech content is also recorded by the video camera system 122. In some implementations, the video camera system 122 includes an annotation interface via which an analyst analyzes video recordings from the camera and annotates the video or a separate data log indicating bodily movement information of the interviewer 102 and the interviewee 104.

Figure 2:
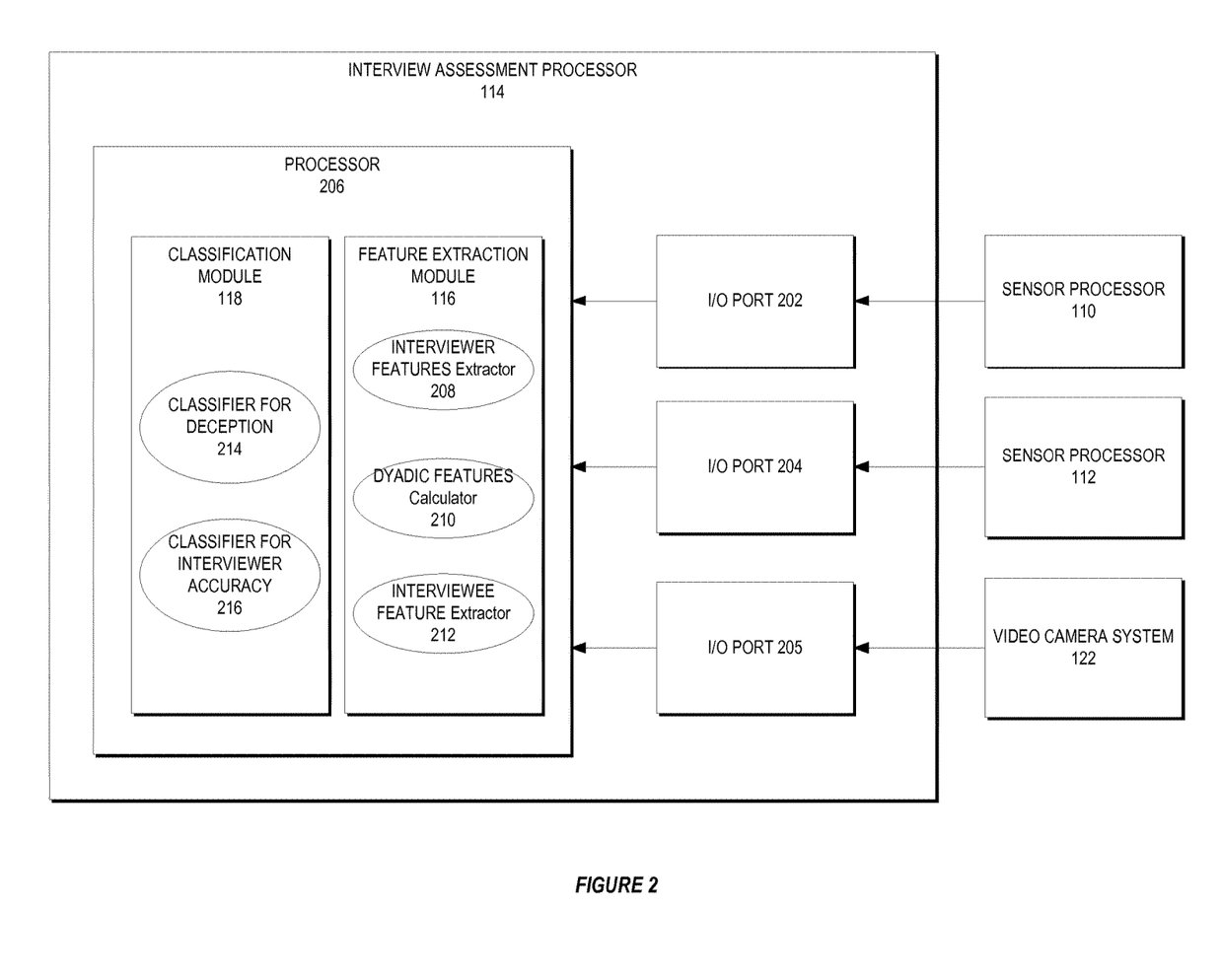
FIG. 2 illustrates a block diagram of the example interview assessment system from FIG. 1.

FIG. 2 illustrates a block diagram of the interview assessment processor 114. The interview assessment processor includes a plurality of I/O ports 202, 204, and 205, and the processor 206, which further includes the feature extraction module 116 and the classification module 118.

The interview assessment processor 114 includes a plurality of I/O ports 202, 204, and 205. The I/O ports 202 and 204 enable the physiological and bodily movement information of the interviewer 102 and the interviewee 104 to be transferred from the sensor processors 110 and 112 to the processor 206. The I/O port 205 enables the processor 206 to receive data from the video camera system 122. In some implementations, the I/O ports are USB, optical, Bluetooth, WiFi, cellular or other digital connection ports.

The interview assessment processor 114 includes a processor 206. The processor 206 can be a general purpose processor executing computer executable instructions, which when executed carry out the functionality described herein. In other implementations, the processor 206 can be or can include special purpose circuitry such as an application-specific integrated circuit (ASIC) or a field-programmable gate array (FPGA), configured specifically for carrying out the functionality described herein. In some implementations, the modules of the processor 206 are implemented as processor executable instructions stored in memory coupled to the processor 206 which are executed by the processor 206.

As described above, the processor 206 of the interview assessment processor 114 includes the feature extraction module 116 and the classification module 118 shown in FIG. 1. The feature extraction module 116 includes an interviewer feature extractor 208, an interviewee feature extractor 212, and a dyadic feature calculator 210. The interviewer feature extractor 208 extracts features (or objective metrics) of the interviewer's physiological and bodily movement signals received from the sensor processor 110 and the video camera system 122. Likewise, the interviewee feature extractor 212 extracts features (or objective metrics) of the interviewee's physiological and bodily movement signals received from the sensor processor 112 and the video camera system 122. The dyadic feature calculator 210 calculates metrics based on features extracted from signals collected from both the interviewer and the interviewee. In some implementations, both baseline data collected before the interview (e.g., 5 minutes before the interview) and the data collected during the interview are used by the interviewer feature extractor 208, the interviewee extractor 212, and the dyadic feature calculator 210 to calculate data features used to assess interviewer accuracy and interviewee deceptiveness.

Generally speaking, extracted or calculated features are interviewee-specific, interviewer-specific, or dyadic. In other words, the interviewer feature extractor 208 extracts interviewer-specific features; the interviewee feature extractor 212 extracts interviewee-specific features; the dyadic feature calculator 210 calculates dyadic features based on the features extracted from signals collected from both the interviewer and the interviewee. Dyadic features characterize the nature of interactions within the pair. In some implementations, one or more dyadic features may indicate a degree of coherence between similar interviewer and interviewee features. In some implementations, one or more dyadic feature may indicate a degree of influence (i.e., leading or following) between similar interviewer and interviewee features.

In some implementations, categories of features extracted from the interviewer's physiological signals and the interviewee's physiological signals include, but are not limited to, interviewer- and interviewee-specific time-domain ECG measures based on intervals between consecutive normal sinus beats (NN), interviewer- and interviewee-specific frequency-domain ECG measures based on NN, interviewer- and interviewee-specific complexity (multiscale entropy) ECG measures, dyadic complexity ECG measures, interviewer- and interviewee-specific mutual information (shannon entropy) ECG measures, dyadic mutual information ECG measures, interviewer- and interviewee-specific heart rate measures, and dyadic ECG measures obtained using autoregressive integrated moving average (ARIMA) analyses. Each category of features is described in detail below.

In some implementations, the interviewer- and interviewee-specific time-domain ECG measures based on NN include, but are not limited to, a percentage of differences between adjacent NN intervals that are greater than 20 milliseconds (referred to as "pNN20") and a ratio of mean heart rate during the interview to the pNN20 metric (referred to as "HR/pNN20"). HR/pNN20 is a possible "stress index," where a higher value of HR/pNN20 indicates greater sympathetic tone and lower parasympathetic tone, and a higher estimated level of stress. In some implementations, the interviewer- and interviewee-specific time-domain ECG measures based on NN include a sample entropy measure with data points of length m=2 and tolerance r=20 millisecond. Sample entropy is a measure of complexity—a conditional probability measure quantifying the likelihood that if a sequence of m consecutive data points matches (within a tolerance r) a template sequence of the same length, then the two will still match when their length increases from m to m+1 data points. Sample entropy quantifies the degree of irregularity of a time series. In some implementations, the interviewer- and interviewee-specific time-domain ECG measures based on NN include a change in average NN-intervals from a baseline to an interview, an average NN-interval during a baseline, an average NN-interval during an interview, a standard deviation of all NN intervals, a standard deviation of the averages of NN-intervals in 5 minute non-overlapping windows of data, a mean of the standard deviations of NN-intervals in 5 minute non-overlapping windows of data, and a square root of the mean of the squares of differences between adjacent NN-intervals.

In some implementations, the interviewer- and interviewee-specific frequency-domain ECG measures based on NN include, but are not limited to, total spectral power of all NN intervals of the following ranges: up to 0.003 Hz, between 0.003 and 0.04 Hz, between 0.04 and 0.15 Hz, between 0.15 and 0.4 Hz, and up to 0.04 Hz. In some implementations, the interviewer- and interviewee-specific frequency-domain ECG measures based on NN include a ratio of low to high frequency power.

In some implementations, the interviewer- and interviewee-specific complexity (multiscale entropy) ECG measures include, but are not limited to, a multiscale sample entropy complexity index measure. The multiscale sample entropy measure is calculated based on three steps. The first step is to derive a set of coarse-grained time-series that represent a system's dynamics over different time scales. The second step is to measure the information content of each of these coarse-grained time series using sample entropy. The third step is to integrate the sample entropy values over a predefined range of scales. For example, a scale of 1 to 9 corresponds to approximately 1 to 9 seconds. Higher multiscale sample entropy values indicate more complex dynamics. In some implementations, for the second step, a sample entropy is calculated based on data points of length m=2 and tolerance r=8 milliseconds or r=15% of the time series' standard deviation. In some implementations, for the third step, the predefined range of scales is 1 second to 9 seconds.

In some implementations, the dyadic complexity ECG measures include, but are not limited to, a 2D-multiscale sample entropy measure and a cross-multiscale sample entropy measure.

A cross-multiscale sample entropy measure is a technique for comparing two different time series to assess their degree of asynchrony or dissimilarity. A cross-multiscale sample entropy measure is calculated according to the following algorithm:

1) given two time series of N data points $\{u(j): 1 \leq j \leq N\}$ and $\{v(j): 1 \leq j \leq N\}$, form vectors $\vec{x}_m(i) = \{u(i+k): 0 \leq k \leq m-1\}$ and $\vec{y}_m(i) = \{v(i+k): 0 \leq k \leq m-1\}$;
2) the distance between two such vectors is defined as: $d[\vec{x}_m(i), \vec{y}_m(j)] = \max\{\|u(i+k)-v(j+k)\|: 0 \leq k \leq m-1\}$;
3) define $B_i^m(r)(v\|u)$ as $(N-m)^{-1}$ times the number of vectors $\vec{y}_m(j)$ within r of $\vec{x}_m(i)$, for $1 \leq j \leq N-m \rightarrow B^m(r)(v\|u) = (N-m)^{-1} \Sigma_{i=1}^{N-m} B_i^m(r)(v\|u)$;
4) define $A_i^m(r)(v\|u)$ as $(N-m)^{-1}$ times the number of vectors $\vec{y}_{m+1}(j)$ within r of $\vec{x}_{m+1}(i)$, for $1 \leq j \leq N-m \rightarrow A^m(r)(v\|u) = (N-m)^{-1} \Sigma_{i=1}^{N-m} A_i^m(r)(v\|u)$;
5) cross-SampEn(m, r, N)$(v\|u) = -\ln(A^m(r)(v\|u)/B^m(r)(v\|u))$,
6) wherein cross-SamEn represents the cross-multiscale sample entropy, $(N-m)B_i^m(r)(v\|u)$ is the number of vectors from v within r of the i-th template of the series u, $\Sigma_{i=1}^{N-m}(N-m)B_i^m(r)(v\|u)$ counts the number of pairs of length m vectors from the two series that match within r, and $\Sigma_{i=1}^{N-m}(N-m)B_i^m(r)(v\|u)$ counts the number of pairs of component vectors of length m+1 from the two series that match within r.

A 2D-multiscale sample entropy measure is a measure of the coordination between two time series. The major differences between a 2D-multiscale sample entropy measure and a multiscale sample entropy measure reside in the way the vectors are defined and how the distance between them is calculated. A 2D-multiscale sample entropy measure is calculated according to the following equations:

for two time series of N data points, $X = \{x_1, \ldots, x_N\}$ and $Y = \{y_1, \ldots, y_N\}$, the vectors are concatenated, creating vectors of the form: $v_m(i) = \{x_i, \ldots, x_{i+m-1}, y_i, \ldots, y_{i+m-1}\}$, $1 \leq i \leq N-m$;

the distance between two vectors in 2D-multiscale sample entropy is defined as: $d[v_m(i)-v_m(j)] = \max_{l=1, \ldots, m} \{|x_{i+l+1}-y_{j+l-1}| \leq r, l \neq j\}$.

In some implementations, the interviewer- and interviewee-specific mutual information (shannon entropy) ECG measures include, but are not limited to, a entropy measure of inter-heartbeat interval (IBI) during a baseline data collection, a entropy measure of IBI during a baseline data collection that is normalized for comparison across dyads, a entropy measure of IBI during an interview, a entropy measure of IBI during an interview that is normalized for comparison across dyads.

In some implementations, the dyadic mutual information ECG measures include, but are not limited to, mutual information between interviewee-and-interviewer time synced instantaneous heart rate signals during an interview. To create the time synced instantaneous heart rate signals, the respective IBI signals for the interviewer and interviewee can be interpolated and uniformly resampled, for example, using a standard moving window interpolation method. Such time synced signals can also be analyzed using ARIMA or various mean square error (MSE) analyses.

In some implementation, the interviewer- and interviewee-specific heart rate (HR) measures include, but are not limited to, a change in mean HR from a baseline to an interview, a mean HR during a baseline data collection, a mean HR during an interview, a change in standard deviation of HR from a baseline to an interview, a HR standard deviation during a baseline, and a HR standard deviation during an interview.

In some implementations, the dyadic ECG measures with ARIMA analyses include, but are not limited to, a multiple correlation coefficient between interviewer and interviewee time series residuals, a squared multiple correlation coefficient between interviewer and interviewee time series residuals, a standardized regression coefficient between interviewer and interviewee time series residuals, an unstandardized regression coefficient for the model in which the interviewee's time series was used as the dependent variable, an unstandardized regression coefficient for the model in which the interviewer's time series was used as the dependent variable, a multiple correlation coefficient for the model in which the interviewee was predicting the interviewer's time series, a squared multiple correlation coefficient for the model in which the interviewee was predicting the interviewer's time series, a standardized regression coefficient for the model in which the interviewee was predicting the interviewer's time series, an unstandardized regression coefficient for the model in which the interviewee was predicting the interviewer's time series, a multiple correlation coefficient for the model in which the interviewer was predicting the interviewee's time series, a squared multiple correlation coefficient for the model in which the interviewer was predicting the interviewee's time series, a standardized regression coefficient for the model in which the interviewer was predicting the interviewee's time series, and an unstandardized regression coefficient for the model in which the interviewer was predicting the interviewee's time series.

In some implementations, categories of features extracted from the interviewer's nonverbal bodily movement (NVB) signals and the interviewee's nonverbal bodily movement signals include, but are not limited to, interviewer- and interviewee-specific or dyadic activity measures which capture statistical information about frequency and durations of NVBs, dyadic mimicry measures which capture start/stop NVB relationships between the interviewer and the interviewee, and dyadic influence model measures which capture temporal NVB relationships between the interviewer and the interviewee.

In some implementations, the activity measures include, but are not limited to, the fraction of the time of the interview during which the individual performed NVBs when all NVBs are considered, the fraction of the time of the interview during which the individual performed hand/finger NVBs, the fraction of the time of the interview during which the interviewee and the interviewer performed NVBs simultaneously when all NVBs are considered, the fraction of the time of the interview during which the interviewee and the interviewer performed NVBs simultaneously when only hand/finger NVBs are considered, the average amount of time the individual performed NVBs—computed as the average duration of all distinct NVB intervals when all NVBs are considered, and the average length of distinct NVB intervals when only hand/finger NVBs are considered. As described above, for the activity measures, in some implementations, all nonverbal bodily movements of the interviewer and the interviewee are considered; in other implementations, only hand and/or finger movements of the interviewer and the interviewee are considered.

In some implementations, the mimicry measures include, but are not limited to, the number of times the interviewer initiated a NVB within 2 seconds of the interviewee ending a NVB—calculated as the number of times per minute when all NVBs are considered, the number of times the interviewee initiated a NVB within 2 seconds of the interviewer ending a NVB—calculated as the number of times per minute when all NVBs are considered, the number of times the interviewer initiated a NVB within 2 seconds of the interviewee ending a NVB—calculated as the number of times per minute when only hand/finger NVBs are considered, number of times the interviewee initiated a NVB within 2 seconds of the interviewer ending a NVB—calculated as the number of times per minute when only hand/finger NVBs are considered, the number of times the interviewer initiated a NVB within 2 seconds of the interviewee ending a NVB—calculated as the number of times per minute when only leg/hand NVBs are considered, the number of times the interviewee initiated a NVB within 2 seconds of the interviewer ending a NVB—calculated as the number of times per minute when only leg/hand NVBs are considered. As described above, for the mimicry measures, in some implementations, all nonverbal bodily movements of the interviewer and the interviewee are considered; in alternative implementations, only hand and/or finger movements of the interviewer and the interviewee are considered; in other implementations, only leg and/or hand movements of the interviewer and the interviewee are considered.

In some implementations, the influence model measures include, but are not limited to, the influence of the interviewee's NVBs on interviewer's NVBs when all NVBs are considered—referred to as "Sub_Inf_Int_1," the influence of the interviewer's NVBs on the interviewee's NVBs when all NVBs are considered—referred to as "Int_Inf_Sub_1," the difference between Sub_Inf_Int_1 and Int_Inf_Sub_1, the interviewee's influence on the interviewer when only hand/finger NVBs movements are considered—referred to as "Sub_Inf_Int_2," the interviewer's influence on the interviewee when only hand/finger NVBs are considered—referred to as "Int_Inf_Sub_2," the difference between Sub_Inf_Int_2 and Int_Inf_Sub_2, the interviewee's influence on the interviewer when only leg/hand NVBs are considered—referred to as "Sub_Inf_Int_3," the interviewer's influence on the interviewee when only leg/hand NVBs are considered—referred to as "Int_Inf_Sub_3," and the difference between Sub_Inf_Int_3 and Int_Inf_Sub_3. As described above, for the influence model measures, in some implementations, all nonverbal bodily movements of the interviewer and the interviewee are considered; in alternative implementations, only hand and/or finger movements of the interviewer and the interviewee are considered; in other implementations, only leg and/or hand movements of the interviewer and the interviewee are considered.

In some implementations, for the influence model measures, NVBs are translated into time-synced sequences of binary values for the interviewee and the interviewer, representing on/off of NVBs at 4 Hz. Specifically, each individual's NVB time-series is converted to a binary string of 1's and 0's, where '1' indicates that he was performing the NVB in that interval. The interval can range, for example, from between about 0.125 seconds to about 1.0 seconds. In some implementations, the interval is 0.25 seconds. The two binary strings are modeled as 2-state Markov Chains in a coupled Hidden Markov Model configuration. As known to a person of ordinary skill in the art, a component of a coupled Hidden Markov Model is an interaction parameter. The interaction parameter, typically a value between 0.0 and 1.0, is indicative of the degree to which values in each of the two data streams represented in the coupled Hidden Markov Model influences the values of the other data stream. Accordingly, in some implementations, the dyadic feature calculator uses the interaction parameter of the coupled Hidden Markov Model generated based on the NVB data collected from the interviewer and the interviewee as an influence model measure.

In some implementations, different features are extracted from each of the different physiological or bodily movement signals. In some implementations, multiple features are extracted from one or more of the physiological or bodily movement signals. For example, the standard deviation and the average value may be extracted for heart rate.

In some implementations, the various features can have different time scales.

The classification module 118 of the processor 206 includes a classifier for deception 214 and a classifier for interviewer accuracy 216. The classifier for deception 214 calculates whether the interviewee was being deceptive. The classifier for interviewer accuracy 216 calculates the accuracy of the interviewer. In some implementations, the classifications result in a binary decision. In other implementations, the classifications result in a likelihood or a probability value. As described in detail below, in some implementations, the classifications are calculated based on more than one variable/feature (i.e., they are multivariate classifications).

In some implementations, multivariate model building and feature selection is implemented for classification. Specifically, sequential forward selection techniques and genetic search algorithms are applied to identify the most discriminatory feature categories for deception detection and interviewer accuracy. In some implementations, optimal feature subsets are identified for 2, 3, and 4-dimensional models. In some implementation, more than 100 features are provided to a genetic search algorithm. Through genetic algorithm data mining, subsets of discriminatory feature categories are identified. And then, through exhaustive search, feature combinations with maximum classification accuracy for deception detection and interviewer accuracy are identified.

Figure 3:
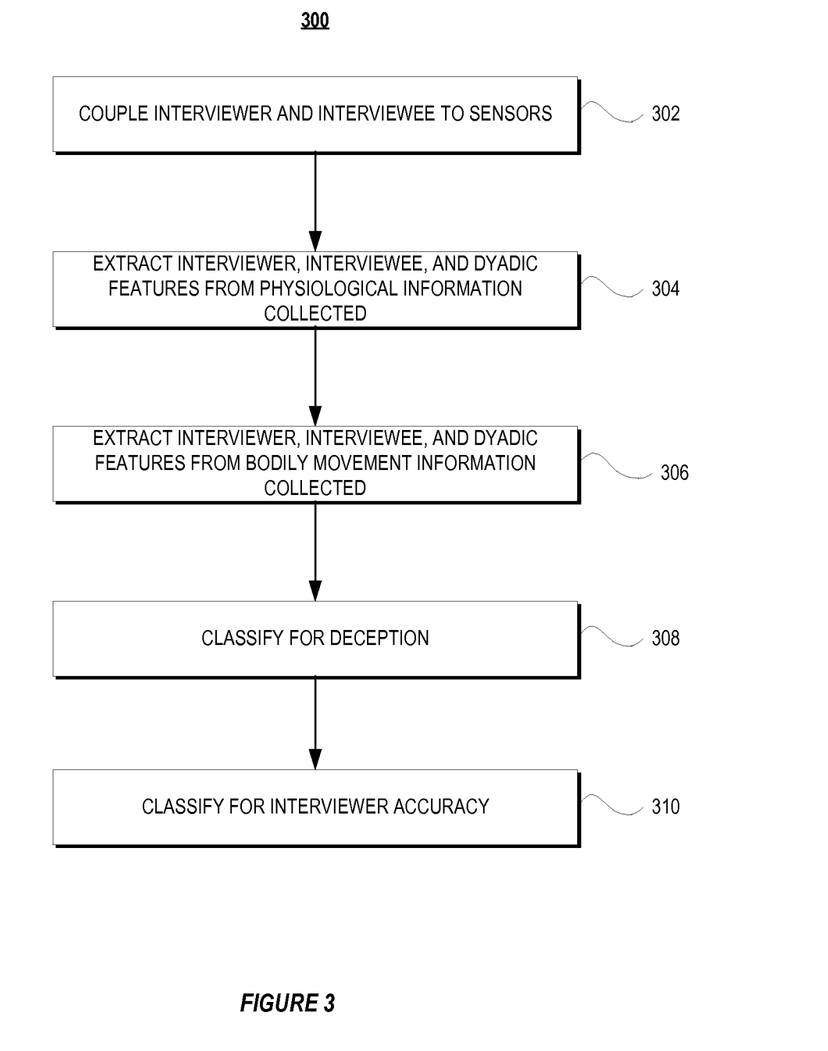
FIG. 3 illustrates a flow chart of an example method for assessing an interview using the system illustrated in FIG. 1.

FIG. 3 illustrates a flow chart of an example method 300 for assessing an interview. The method 300 includes coupling the interviewer and the interviewee to sensors (step 302). Interviewer-specific features, interviewee-specific features, and dyadic features are obtained based on physiological information collected from the interviewer and the interviewee (step 304). Additionally, interviewer-specific features, interviewee-specific features, and dyadic features are obtained based on bodily movement information collected from the interviewer and the interviewee (step 306). The features are then provided to the classifier to classify for deception (step 308) and for interviewer accuracy (step 310).

The method 300 includes coupling an interviewer and an interviewee to a plurality of sensors (step 302). As described above, the sensors record physiological and bodily movement information from the interviewer and the interviewee, and the physiological and bodily movement information is processed by the sensor processors. The physiological information may include, but is not limited to, the physiological parameters discussed above, including measures of cardiac, respiratory, and brain activity. The bodily movement information may include, but is not limited to, leg/foot and hand/finger movements. Bodily movement information can also be obtained from video of an interview.

At step 304, interviewer-specific features, interviewee-specific features, and dyadic features are extracted from physiological information collected from the interviewer and the interviewee. As described above, examples of the interviewer-specific and interviewee-specific features based on physiological information include a change of standard deviation of heart rate from a baseline to an interview, a mean value of heart rate during an interview, an average value of intervals between consecutive normal beats during an baseline, a shannon entropy of inter-beat intervals during an interview, a multiscale entropy of inter-beat intervals during an interview. Also as described above, an example of a dyadic feature of physiological information is interviewee-and-interviewer time synced instantaneous heart rate signals during an interview. Other examples of dyadic features based on physiological information are dyadic ECG measures obtained using ARIMA analyses.

At step 306, interviewer-specific features, interviewee-specific features, and dyadic features are extracted from bodily movement information collected from the interviewer and the interviewee. As described above, for example, an extracted interviewer-specific or interviewee-specific NVB feature may be the fraction of the time of the interview during which the individual performed hand/finger NVBs. Dyadic NVB features may include an influence metric indicating whether the interviewer's NVB feature signal appears to lead or follow the interviewee's NVB feature signal. In more detail, the influence metric may be the number of times the interviewer initiated a nonverbal bodily movement within, for example, two seconds of the interviewee ending a nonverbal bodily movement, or the fraction of the time the interviewer and the interviewee performed nonverbal bodily movements simultaneously.

At steps 308 and 310, features extracted from steps 304 and 306 are then used (as input to the classifiers) to classify for deception and interviewer accuracy. As described above, the classification may result in a binary decision, a likelihood or a probability value. Also as described above, in some implementations, the classification is calculated based on more than one feature.

Figure 4:
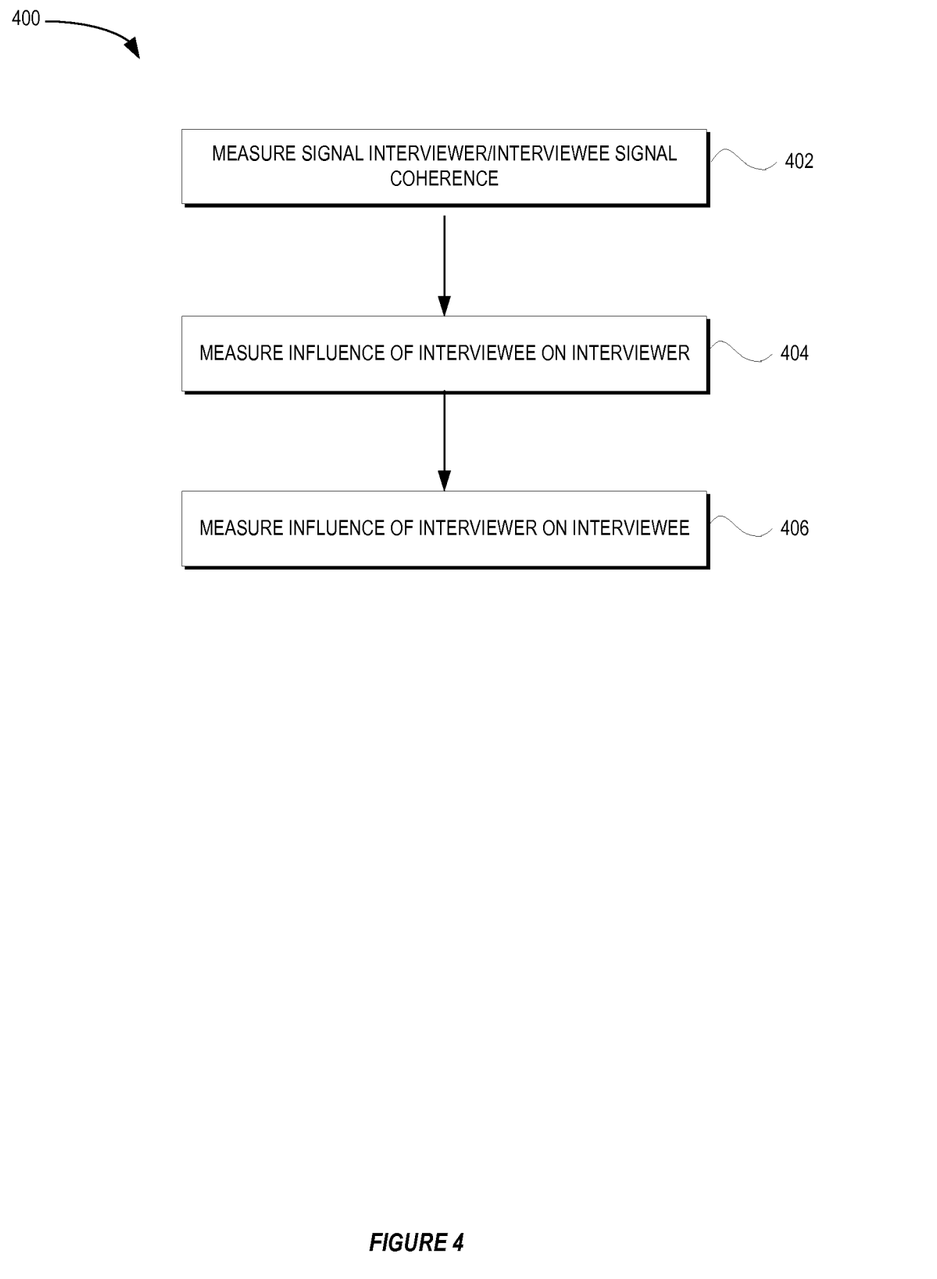
FIG. 4 illustrates a flow chart showing an example method for obtaining certain dyadic features suitable for use in determining interviewer accuracy and interviewee deceptiveness.

FIG. 4 illustrates a flow chart showing an example method 400 for obtaining certain dyadic features suitable for use in determining interviewer accuracy and interviewee deceptiveness. In some implementations, it was found that features measuring the degree of coherence between an interviewer signal and an interviewee signal was a significant dyadic feature in the analysis of interviewer accuracy and interviewee deceptiveness. In some implementations, a dyadic influence measure was found to be a significant dyadic feature to be used instead of or in addition to signal coherence. Accordingly, the method includes processing time-synced signals of the interviewer and the interviewee to identify a degree of coherence between the signals (step 402). A time lag is applied to the physiological signal of the interviewer and compared to the original interviewee signal to determine the degree to which the interviewee influences the interviewer (step 404). A time lag is applied to the physiological signal of the interviewee and compared to the original interviewer signal to determine the degree to which the interviewer influences the interviewee (step 406).

As indicated above, the method 400 includes determining a degree of coherence between a physiological signal of the interviewer with a corresponding physiological signal of the interviewee (step 402). In some implementations, the signals compared are the ECG signals (or a processed version thereof, e.g., an inter-beat interval signal) of the interviewer and interviewee, though in other implementations, other physiological signals can be used instead. The coherence between the two signals can be computed in a number of ways, including via auto-regressive integrated moving average (ARIMA) modeling and through mutual information (MI) analysis. As known to persons of ordinary skill in the art, ARIMA analysis involves generating a model of a signal which removes patterns of autocorrelation leaving a set of residuals. After the ARIMA models of the signals are generated, the residuals are submitted to regression analysis. The significance of the regression coefficients correlates to the degree of coherence between the two signals. MI analysis can yield a similar coherence measure.

Similar analyses are conducted with a time-lagged version of the interviewer signal (step 404). If ARIMA modeling is used, a new ARIMA model can be generated for the time lagged interviewer signal, and its residuals can be compared to the residuals of the ARIMA model of the non-time-lagged interviewee signal. If MI analysis is used, the time-lagged interviewer signal can be processed directly with an MI evaluation with the non-time-lagged interviewee signal. The degree of lag can range from between about 0.5 s to about 5.0 s. In some implementations, several different time lags can be evaluated and used as separate features. In some implementations, multiple time-lags can be calculated and the time signal with the greatest correlation or MI value can be used as the feature. In general the comparison between the time-lagged interviewer signal and the interviewee signal indicates a degree to which the interviewee signal influences the interviewer signal. Insignificant regression coefficients or low MI values indicate little influence, where more significant regression coefficients or high MI values indicate a higher degree of influence.

An analysis is also conducted of a time-lagged version of the interviewee signal with respect to the non-time lagged interviewer signal (step 406). The analysis can be conducted as described above in relation to step 404, with the time lag being applied to the interviewee signal instead of the interviewer signal. This analysis indicates the degree to which the interviewer signal influences the interviewee signal.

While the method 400 includes analyzing the coherence, and mutual degrees of influence of two corresponding interviewer/interviewee signals, in some implementations, only the coherence measure, only one influence measure, or only two of the three comparisons is conducted. In some implementations, the above signal comparisons can be applied to multiple physiological signals and/or to one or more non-verbal behavior signals.

Experimental Results

Using the techniques described above, experiments were conducted to identify parameters that are particularly effective to assess interviewee deceptiveness and interviewer accuracy. Twenty-five interviewees were selected. Data was collected from 25 dyads (25 interviewees and 4 interviewers). As described above, various interviewer-specific, interviewee-specific and dyadic features were extracted and calculated from each interviewer and each interviewee. Optimal feature subsets were identified for 2, 3, and 4-dimensional models through a genetic search algorithm. Specifically, discriminative feature categories were identified as members of feature subsets in the $95^{th}$ percentile of 'fitness', as determined by 100 iterations of 5-fold cross-validation using a linear classifier. Certain findings are discussed below.

Significant coherence was observed in the majority of the dyads. Although ARIMA and mutual information measure fundamentally different quantities, they both find significance in over half of the dyads. An interviewee who lied tended to lead the interviewer's physiology. That is, the comparison between a physiological signal of an interviewee compared with a time-lagged version of a corresponding interviewer signal tended to be a significant indicator of deception. An interviewer who was incorrect in predicting his accuracy tended to lead the interviewee's physiology and strongly influenced the interviewee's nonverbal bodily movements. That is, the comparison between physiological signals and non-verbal bodily movement signals of an interviewer compared with time-lagged versions of corresponding interviewee signals tended to be a significant indicator of inaccuracy.

Multivariate models for deception detection and interviewer accuracy demonstrate that a diversity of features contributed to high probability in correct classification. Interviewer signals and features make unique contributions to operational goals and outcomes. Prominent feature categories for deception detection are dyadic ECG measures obtained using ARIMA analyses, mean heart rate measures, dyadic influence model NVB measures (such as coupled Hidden Markov Model interaction parameters), and time-domain ECG measures based on intervals between consecutive normal sinus beats. Prominent feature categories for interviewer accuracy are complexity ECG measures, dyadic ECG measures with ARIMA analyses, time-domain ECG measures based on intervals between consecutive normal sinus beats, and frequency-domain ECG measures based on intervals between consecutive normal sinus beats. Key features for deception detection and interviewer accuracy tend to be uncorrelated and each uniquely contributes to overall performance. Interviewer-specific features may distinguish different classes of interviewers and may also predict efficacy and performance for distinct interviewee groups. Interviewer-specific features allow approaches for efficacious pairing of an interviewer and an interviewee and provide tools for interviewer training and self-improvement.

For deception detection, an example 4-feature model provided an 84.3% probability in correct classification with K-fold cross-validation. The 4-features included the following: 1) a mean baseline (before an interview) heart rate from the interviewee; 2) the interviewee's influence on the interviewer when only the leg and hand movements of the interviewer and the interviewee are measured; 3) with ARIMA analysis, a squared multiple correlation coefficient for the module in which the interviewee is predicting the interviewer's time series residuals; and 4) with ARIMA analysis, a squared multiple correlation coefficient for the module in which the interviewer is predicting the interviewee's time series residuals.

For interviewer accuracy, an example 4-feature model provided an 86.1% probability in correct classification with K-fold cross-validation. The 4-features include: 1) a multi-scale entropy complexity index measure of the interviewer's ECG wherein the predefined range of scales is 1 second to 9 seconds, and the sample entropy has data points of length m=2 and tolerance r=15% of the time series' standard deviation; 2) with ARIMA analysis, a squared multiple correlation coefficient between interviewer and interviewee time series residuals; 3) a change in standard deviation of interviewer's heart rate from a baseline to an interview; and 4) a standard deviation of interviewee's consecutive normal sinus beat intervals obtained from ECG during an interview.

The above two models are merely examples of several 2, 3, or 4-feature models that were identified which provide high levels of accuracy in both deception detection and assessment of interviewer accuracy.

The invention may be embodied in other specific forms without departing from the spirit or essential characteristics thereof. The forgoing implementations are therefore to be considered in all respects illustrative, rather than limiting of the invention.

What is claimed is:

1. A method of detecting deception by an interviewee and predicting accuracy by an interviewer in an interview conducted by the interviewer, comprising:
   recording, by at least a first sensor, a first time series of physiological data comprising electrocardiogram data of the interviewer during the interview;
   recording, by at least a second sensor, a second time series of physiological data comprising electrocardiogram data of the interviewee during the interview;
   generating, by a computer, a time lagged time series comprising the second time series of physiological data shifted a predetermined length of time;
   determining, by the computer, a dyadic feature based on the first time series of physiological data comprising electrocardiogram data of the interviewer and the time lagged time series of the interviewee, wherein the dyadic feature indicates at least one of a time-based or frequency-based relationship between the first time series of physiological data comprising electrocardiogram data of the interviewer and the time lagged time series of the interviewee;
   determining, by the computer and based on the dyadic feature, a level of coherence between the first time series of physiological data and the second time series of physiological data; and
   generating, by the computer, an accuracy score for the interviewer based on the level of coherence between the first time series of physiological data and the second time series of physiological data being above a predetermined threshold.

2. The method according to claim 1, further comprising recording at least one of skin conductance data and pulse oximetry data of the interviewer or the interviewee.

3. The method according to claim 1, further comprising calculating a level of entropy, a heart rate, and time intervals between consecutive normal sinus beats in the first time series and the second time series.

4. The method according to claim 1, further comprising:
   applying an auto-regressive integrated moving average analysis to the first time series of physiological data of the interviewer and the second time series of physiological data of the interviewee.

5. The method according to claim 1, further comprising:
   recording a third time series comprising movement data of the interviewer during the interview;
   recording a fourth time series comprising movement data of the interviewee during the interview;
   determining, by the computer, the level of coherence between the third time series comprising the movement data of the interviewer and the fourth time series comprising the movement data of the interviewee.

6. The method according to claim 5, further comprising:
   recording video of the interview; and
   processing the recorded video to generate the third time series comprising the movement data of the interviewer and the fourth time series comprising the movement data of the interviewee.

7. The method according to claim 5, wherein the third time series comprising the movement data of the interviewer and the fourth time series comprising the movement data of the interviewee indicate times at which the interviewer and interviewee, respectively, moved their respective limbs or appendages.

8. The method according to claim 5, wherein the determining by the computer at least one of an influence relationship or the level of coherence between the third time series comprising the movement data of the interviewer and the fourth time series comprising the movement data of the interviewee comprises modelling the third time series comprising the movement data of the interviewer and the fourth time series comprising the movement data of the interviewee as a coupled Hidden Markov Model.

9. A system of detecting deception by an interviewee and predicting accuracy by an interviewer in an interview conducted by the interviewer, comprising:
a first sensor to record a first time series of physiological data comprising electrocardiogram data of the interviewer during the interview;
a second sensor to record a second time series of physiological data comprising electrocardiogram data of the interviewee during the interview;
a processor to:
generate a time lagged time series comprising the second time series of physiological data shifted a predetermined length of time;
determine a dyadic feature based on the first time series of physiological data comprising electrocardiogram data of the interviewer and the time lagged time series of the interviewee, wherein the dyadic feature indicates at least one of a time-based or frequency-based relationship between the first time series of physiological data comprising electrocardiogram data of the interviewer and the time lagged time series of the interviewee;
determine, based on the dyadic feature, a level of coherence between the first time series of physiological data and the second time series of physiological data; and
generate an accuracy score for the interviewer based on the level of coherence between the first time series of the physiological data and the second time series of physiological data being above a predetermined threshold.

10. The system according to claim 9, further comprising:
a third sensor to record skin conductance data or pulse oximetry data of the interviewer or the interviewee.

11. The system according to claim 9, further comprising the processor to calculate a level of entropy, a heart rate, and time intervals between consecutive normal sinus beats in the first time series and the second time series.

12. The system according to claim 9, further comprising the processor to
apply an auto-regressive integrated moving average analysis to the first time series of physiological data of the interviewer and the second time series of physiological data of the interviewee.

13. The system according to claim 9, wherein, when the processor determines the level of coherence between a third time series comprising bodily motions of the interviewer and a fourth time series comprising bodily motions of the interviewee.

14. The system according to claim 13, further comprising:
a video recording device to record a video of the interview; and
the processor to process the recorded video to generate the third time series comprising the bodily motions of the interviewer and the fourth time series comprising the bodily motions of the interviewee.

15. The system according to claim 14, further comprising the processor to determine at least one of the influence relationship or the level of coherence between the third time series comprising the bodily motions of the interviewer and the fourth time series comprising the bodily motions of the interviewee with a coupled Hidden Markov Model.

16. The system according to claim 14, wherein the third time series comprising the bodily motions of the interviewer and the fourth time series comprising the bodily motions of the interviewee indicate times at which the interviewer and interviewee, respectively, moved their respective limbs or appendages.

17. A non-transitory computer readable medium storing a computer-readable program to detect deception by an interviewee and predicting accuracy by an interviewer in an interview conducted by the interviewer, wherein execution of the computer-readable program by at least one processor cause the at least one processor to:
record, from at least a first sensor, a first time series of physiological data comprising electrocardiogram data of the interviewer during the interview;
record, from at least a second sensor, a second time series of physiological data comprising electrocardiogram data of the interviewee during the interview;
generate a time lagged time series comprising the second time series of physiological data shifted a predetermined length of time;
determine a dyadic feature based on the first time series of physiological data comprising electrocardiogram data of the interviewer and the time lagged time series of the interviewee, wherein the dyadic feature indicates at least one of a time-based or frequency-based relationship between the first time series of physiological data comprising electrocardiogram data of the interviewer and the time lagged time series of the interviewee;
determine, based on the dyadic feature, a level of coherence between the first time series of physiological data and the second time series of physiological data; and
generate an accuracy score for the interviewer based on the level of coherence between the first time series of the physiological data and the second time series of physiological data being above a predetermined threshold.

18. The non-transitory computer readable medium according to claim 17, wherein execution of the computer-readable program by the at least one processor cause the at least one processor to determine the level of coherence between a third time series comprising movement data of the interviewer and a fourth time series comprising movement data of the interviewee.

* * * * *